US 6,730,030 B2

(12) United States Patent
Palti (10) Patent No.: US 6,730,030 B2
(45) Date of Patent: May 4, 2004

(54) METHOD AND APPARATUS FOR DETECTING ARTERIAL STENOSIS

(76) Inventor: Yoram Palti, 51 Ruth Street, Haifa 34404 (IL)

( * ) Notice: Subject to any disclaimer, the term of this patent is extended or adjusted under 35 U.S.C. 154(b) by 0 days.

(21) Appl. No.: 10/085,517

(22) Filed: Feb. 28, 2002

(65) Prior Publication Data

US 2002/0151795 A1 Oct. 17, 2002

Related U.S. Application Data

(60) Provisional application No. 60/273,776, filed on Mar. 2, 2001.

(51) Int. Cl.⁷ .................................................. A61B 8/12

(52) U.S. Cl. ....................................... 600/441; 600/453

(58) Field of Search .................................. 600/407–471, 600/481, 485, 500–502, 504, 528; 73/620–626, 630, 631, 861.01, 592; 367/7, 11, 130, 138; 128/916, 898; 378/4, 17, 901; 601/2, 3; 382/107, 128

(56) References Cited

U.S. PATENT DOCUMENTS

| 4,476,874 A | 10/1984 | Taenzer et al. ............. 128/663 |
| 4,719,923 A | 1/1988 | Hartwell et al. ............ 128/663 |
| 4,770,184 A | 9/1988 | Greene, Jr. et al. ...... 128/661.08 |
| 4,961,427 A | 10/1990 | Namekawa et al. ... 128/661.09 |
| 4,975,856 A | 12/1990 | Vold et al. .................... 364/513 |
| 5,327,893 A | 7/1994 | Savic ...................... 128/661.08 |
| 5,383,463 A | 1/1995 | Friedman ................ 128/661.09 |
| 5,579,771 A | * 12/1996 | Bonnefous .................. 600/450 |
| 5,623,929 A | 4/1997 | Weng ...................... 128/661.09 |
| 5,701,898 A | 12/1997 | Adam et al. ............ 128/661.09 |
| 6,048,319 A | * 4/2000 | Hudgins et al. ............. 600/528 |
| 6,503,205 B2 | 1/2003 | Manor et al. ................ 600/459 |

FOREIGN PATENT DOCUMENTS

| WO | WO 98/23211 | 6/1998 | ................. 600/459 |
| WO | WO 00/28899 | 5/2000 | ............ A61B/8/06 |

OTHER PUBLICATIONS

Agur, Anne MR, Grant's Atlas of Anatomy, Ninth Edition, Williams & Wilkins, London, 1991, pp. 47–50.
Boucek, Robert et al., Coronary Artery Disease Pathologic and Clinical Assessment, Williams & Wilken, London, 1984, pp. 131–140.
Fung, Y.C., Biodynamics; Circulation, Springer Verlag, Berlin, 1984, pp. 143–144.
Gill, Robert W., Measurement of Blood Flow by Ultrasound: Accuracy and Sources of Error, Ultrasound Med Biol, vol 11(4), 1985, pp. 625–641.
Hwang Ned, PhD, Normann Nils, Cardiovascular Flow Dynamics and Measurements, University Park Press, London, 1977, pp. 550–552.
Marcus, Melvin, The Coronary Circulation in Health and Disease, McGraw Hill Book Company, Hamburg, 1983, pp. 242–269.

(List continued on next page.)

Primary Examiner—Ali Imam
(74) Attorney, Agent, or Firm—David M. Klein; Shearman & Sterling LLP (57) ABSTRACT

A Doppler ultrasound system automatically and repeatedly scans an area of interest to construct at least one velocity profile through segments of arteries over an area of interest. Each scan includes taking measurements of blood flow in the area of interest substantially simultaneously from different angles. The velocity profiles and delta velocity profiles are automatically analyzed to determine a number of parameters indicative of potentially stenotic areas within the artery. The parameters and their changing value along the length of the artery indicative of stenosis are detected and compared with predefined threshold values to determine potentially stenotic areas. Scanning by the Doppler ultrasound system is triggered at a predefined point in an ECG cycle of the patient.

34 Claims, 8 Drawing Sheets

OTHER PUBLICATIONS

Nichols, Wilmer W, O'Rourke, Michael F., McDonald's Blood Flow in Arteries, Third Edition, Lea & Febiger, London, 1990, p. 45.

Nichols, Wilmer W, O'Rourke, Michael F., McDonald's Blood Flow in Arteries, Fourth Edition, Arnold, London, 1998, pp. 11–17, 155–169, 317–331, and 396–401.

Roberts, Colin Dr., Blood Flow Measurement, Sector Publishing Limited, London, 1972, pp. 13–27.

Powis, Raymond L., Practical Doppler Ultrasound for the Clinician, Willams & Wilkins, Baltimore, 1991, pp. 58–59, 138, 149 and 150.

Schilt et al., The Effects of Time Varying Curvature on Velocity Profiled in a Model of the Coronary Arteries, Journal of Biomechanics, vol. 29, No. 4, 1996, pp. 469–474.

Sigel Bernard, A Brief History of Doppler Ultrasound in the Diagnosis of Peripheral Vascular Disease, Ultrasound in Med. & Biol., vol. 24, No. 2, 1998, pp. 169–176.

Vieli A, Jenni R., Anliker M, Spatial Velocity Distributions in the Ascending Aorta of Healthy Humans and Cardiac Patients, IEEE Trans. Biomed Eng, vol 33(1), 1986, pp. 28–34.

* cited by examiner

METHOD AND APPARATUS FOR DETECTING ARTERIAL STENOSIS

CROSS-REFERENCE TO RELATED APPLICATION

The present application claims the benefit of Provisional Application Ser. No. 60/273,776, filed Mar. 2, 2001, the contents of which are incorporated by reference herein in their entirety.

BACKGROUND OF THE INVENTION

1. Field of the Invention

The present invention relates generally to detection of arterial stenosis and more particularly to a high-speed method and apparatus for screening for arterial stenosis in which a Doppler ultrasound system automatically detects parameters indicative of stenosis in the velocity profile of blood flow through the length of an artery without analyzing visual imagery.

2. Description of the Related Art

Arteriosclerosis is a chronic disease characterized by abnormal thickening and hardening of the arterial walls. From a medical point of view, arteriosclerosis affecting the coronary arteries is of most concern. Many coronary heart diseases, including arteriosclerosis, angina, myocardial infarction (MI), and sudden death, depend in a large part on the severity and distribution of obstructive coronary lesions that develop slowly over a period of years and that lead to stenotic arteries. As a result, periodic screening of patients to detect and assess obstructive coronary lesions is vital for the diagnosis, treatment and prevention of coronary disease.

It is well known that blood flow through a segment of healthy artery has a parabolic shaped velocity profile. Upon entering a narrowed segment of an artery, however, blood flow accelerates, thereby increasing the momentum and the kinetic energy of the flow. Substantial energy loss occurs at the exit of the narrow segment of the artery, causing turbulence and vortices at the boundaries of the artery. These phenomena increase with an increase in the magnitude of the stenosis and in the magnitude of normal flow velocity through the artery.

The velocity of blood flow of a person at rest is typically in the range of 30 to 50 cm/sec in healthy coronary arteries with a diameter ranging between 1 to 3 mm. In general, blood flow of a person at rest begins to be affected with an 80 to 90 percent reduction in diameter. For a person experiencing maximum blood flow, typically during strenuous exercise, blood flow may be affected with only a 45 percent reduction in diameter.

One imaging method for direct detection of coronary stenosis is coronary arteriography. This is an expensive invasive imaging procedure that is not practical for routine screening. Other non-invasive imaging methods for performing cardiac screening include computerized axial tomography (CAT) and magnetic resonance imaging (NMI). These procedures use still framed images to determine whether a particular section of artery appears to be obstructed. While non-invasive, these procedures are costly and typically cannot be performed as part of a regular check up.

More recently, ultrasound imaging systems have been employed to detect and measure stenosis in the carotid artery by imaging the blood flow in the artery. Presently available ultrasound systems utilize the Doppler principle. In traditional Doppler ultrasound systems, a transducer directs a beam of ultrasonic energy toward a blood vessel in which blood flow information is desired. Moving blood cells reflect the ultrasound energy, called echoes, and either increase or decrease the frequency of the reflected energy depending on the direction of blood flow and the angle of incidence of the beam. In continuous wave systems, a second transducer receives the echo and detects the frequency shift from which velocity of the blood flow may be calculated. In pulse wave systems, a single transducer is used to direct the beam and receive the echo with a filter sorting out the signals to determine the frequency shift and hence the velocity of blood flow.

One limitation of Doppler ultrasound technology is that such systems can only measure the projection of the velocity flowing in the direction of the beam. If the ultrasound beam is directed perpendicular to the direction of flow, no flow will be recorded. If the beam is pointing at some angle with respect to the flow, the recorded velocity will be lower than the actual velocity to a degree proportional to the cosine of the angle. To overcome this limitation, duplex Doppler ultrasound systems, which allow imaging to be used along with traditional Doppler ultrasound systems, are used so that a region of interest may be "eye-balled" by an ultrasound technician and the beam may either be positioned at an appropriate angle or the angle of measurement may be recorded.

Another problem with the use of ultrasound systems is the presence of "noise" components in the Doppler shift frequency. The walls of blood vessels are dynamic in that they move in phase with a beating heart. During the systolic portion of the cardiac cycle the walls move out and during the diastolic portion the walls move in. These movements result in low and high frequency noise components returning with the echo of the Doppler signal.

Notwithstanding advances made in the art, all of the present methods and devices cannot in practice be used to periodically screen the heart region for potential stenotic areas. In general, these methods and devices rely upon visual imaging systems, which have difficulty forming images of the complex human anatomy, and require slow human visual analysis of each image. Therefore, there exists a need for a simple inexpensive non-invasive method of screening for arterial stenosis using a Doppler ultrasound system that does not rely upon visual imaging and is relatively unaffected by the shortcomings of previous ultrasound systems.

SUMMARY OF THE INVENTION

The present invention is a non-invasive method and apparatus for detecting and measuring the degree of coronary and other arterial stenosis without the need for imaging the artery. In accordance with a first method of the invention, a Doppler ultrasound system scans numerous segments of arteries to construct velocity profiles of blood flow across each segment. The path of the artery is determined based on the topographic location of the arterial flow sections, and the shape and skew of the velocity profiles are measured. A delta velocity profile representing the change in velocity along the length of the mapped artery may also be measured. The velocity profile and delta velocity profile are then analyzed to determine potentially stenotic areas within the artery.

A reference coordinate system is defined on the patient so that the location of the Doppler ultrasound system and potentially stenotic areas may be accurately determined. If desired, a visual Doppler image of potentially stenotic areas of the artery may be displayed a upon detection of stenotic areas or at the end of the scanning process. In a preferred embodiment, velocity profile parameters selected from the group consisting of v, dh, b, n, s, and w (each as described below) or V, DH, B, N, S, individually or in any combination thereof, are compared with predefined threshold values to determine potentially stenotic areas within the artery.

After reconstruction of the arterial paths, changes in the parameters indicated above along the path of the artery are compared with predefined thresholds values to determine potentially stenotic areas. In an alternate embodiment, parameters can be measured in both the diastole and systole stages so that their difference as well as their individual values can be evaluated and compared to predefined thresholds. Scanning by the Doppler ultrasound system may be triggered based on detection of a desired point in time on an ECG of the patient.

The Doppler ultrasound system comprises at least one scanner, and preferably comprises a plurality of scanners. The step of defining a reference coordinate system comprises the step of selecting a reference point on the patient and, if desired, measuring angles of reference between the scanners of the Doppler ultrasound system and the selected reference point. The Doppler ultrasound system may be carried on a robotic arm to facilitate more accurate detection of the position of the ultrasound scanner.

Various parameters of the velocity profile may be analyzed to determine potentially stenotic areas, including:
i) The average velocity (v) of the velocity profile;
ii) The peak change in velocity (dh) across the velocity profile;
iii) The presence and degree of blunt flow (b) found in the velocity profile;
iv) The presence and degree of turbulence (N) found in the velocity profile;
v) The degree of skew (s) in the velocity profile; and
vi) The width (w) of the velocity profile.

After reconstructing the path of the artery based on the individual velocity profiles measured, the change in each of the parameters (v, dh, b, n, s, and w) along the length of the artery is examined to determine potentially stenotic areas. These additional parameters can be defined respectively as: $(\Delta v/\Delta L)_a$, $(\Delta dh/\Delta L)_a$, $(\Delta b/\Delta L)_a$, $(\Delta dh/\Delta L)_a$, $(\Delta s/\Delta L)_a$, and $(\Delta w/\Delta L)_a$ where $\Delta L$ is the distance between two consecutive velocity profiles along the path of an artery, and a is the position along the artery.

An alternative method of detecting arterial stenosis comprises: using a Doppler ultrasound system to measure a plurality of parameters indicative of a potentially stenotic artery; determining from the measured parameters the degree of stenosis in the artery; and scoring the degree of stenosis and determining coordinates of the potentially stenotic artery.

A further alternative method of detecting arterial stenosis comprises: detecting a signal representative of the velocity of blood flow in an artery; on-structing a series of velocity profiles of the blood flow in the artery; based on the velocity profiles, reconstructing the path of the artery; and based on the velocity profiles, their coordinates and changes in the velocity profile along the path of the artery, identifying potentially stenotic areas in the artery. The velocity profiles are used to determine parameters selected from the group consisting of v, dh, b, n, s, and w, and one or more of the parameters is compared with predefined threshold values to determine potentially stenotic areas within the artery. The delta velocity profiles are used to determine parameters selected from the group consisting of $\Delta v/\Delta L$, $\Delta dh/\Delta L$, $\Delta b/\Delta L$, $\Delta n/\Delta L$, $\Delta s/\Delta L$, and $\Delta w/\Delta L$, and one or more of the parameters is compared with predefined threshold values to determine potentially stenotic areas within the artery. Changes in these parameters along the length of the artery $(\Delta v/\Delta L)_a$, $(\Delta dh/\Delta L)_a$, $(\Delta b/\Delta L)_a$, $(\Delta n/\Delta L)_a$, $(\Delta s/\Delta L)_a$, and $(\Delta w/\Delta L)_a$ may also be compared with thresholds to determine stenotic areas.

Another method of detecting arterial stenosis comprises: detecting a defined point in time on an ECG; upon detection of the defined point, scanning an area of interest using a Doppler ultrasound system to construct a series of velocity profiles of blood flow through the length of the arteries present; reconstructing the path of the arteries; analyzing the velocity profiles; and analyzing delta velocity profiles to determine potentially stenotic areas within the arteries.

An apparatus for detecting stenosis of an artery according to the invention comprises a Doppler ultrasound system for scanning a segment of the artery and for receiving echoes of the Doppler ultrasound signal; and a processor for receiving the echoes and for constructing velocity profiles of blood flow through the area of interest. The processor analyzes the velocity profiles to determine potentially stenotic areas within the artery. The system includes means for defining a reference coordinate system relative to the area of interest, with the processor determining a location of the Doppler ultrasound system in the reference coordinate system upon detecting potentially stenotic areas within the artery. A display is provided for displaying a Doppler image of a potentially stenotic area of the artery upon detection of such stenotic areas.

An alternative apparatus for detecting arterial stenosis includes: a Doppler ultrasound system for measuring a plurality of parameters indicative of a potentially stenotic artery; and a processor for determining from the measured parameters the degree of stenosis in the artery. The processor scores the degree of stenosis and determines the coordinates of the potentially stenotic artery.

A further alternative apparatus for detecting arterial stenosis includes: means for detecting a signal representative of the velocity of blood flow in an artery; means for constructing a velocity profile and/or delta velocity profile of the blood flow in the artery; and means for identifying potentially stenotic areas in the artery based on the velocity profile and/or changes of the velocity profile along the length of an artery.

DETAILED DESCRIPTION OF THE INVENTION

The present invention provides a non-invasive method to routinely screen for stenosis using a Doppler ultrasound system 12. In general, to non-invasively detect the presence and degree of stenosis in blood vessels, such as the coronary arteries, Doppler ultrasound system 12 detects the velocity of blood flow through a selected area of interest, and creates a series of velocity profiles of blood flow through the artery or arteries within the area of interest. The series of the velocity profiles measured are later used to reconstruct the path of the artery and the delta velocity curve (the change in velocity along the length of the artery). Certain parameters indicative of potentially stenotic segments are automatically identified by analyzing the velocity profile and the delta velocity profile of blood flow in a segment of the artery. The degree of the stenosis, which is generally associated with specific changes in the velocity profile along the length of the artery, can be estimated from the parameters measured. As a high speed screening tool, the system takes numerous Doppler readings of the area under observation, preferably at different orientations and/or using multiple scanners, and automatically identifies potentially stenotic areas without relying on visual imaging or user intervention. These areas may then be further considered by a technician or doctor using much slower conventional visual imaging.

In general, the velocity of blood flow through an artery accelerates as it reaches a narrowing segment of an artery. This acceleration results in several characteristics of blood flow that may be detected by the present system, including i) a jet stream that can be detected from an increase in Doppler shift frequencies, ii) an increase in the bluntness of the velocity profile across the artery cross section, iii) an increase in the difference in height between the velocity close to the vessel wall and the maximal blunt flow, and iv) turbulence in the post-stenotic segment of the artery due to an abrupt opening of the post-stenotic artery segment. These flow characteristics can be detected either in the diastole stage, systole stage, or by comparing flow characteristics in the different stages of the cardiac cycle.

The preferred embodiment of the invention involves three functional steps: (1) an initialization procedure, which is described generally in FIG. 1, during which the Doppler scanner is positioned in a reference coordinate system that allows the Doppler scanners to be moved while precisely detecting their positions and the location of the echoes received relative to the patient; (2) a screening procedure, described generally in FIG. 2, during which numerous Doppler readings of the area under observation are automatically taken from many different orientations; and (3) a diagnosis procedure, described generally in FIG. 7, in which the system automatically analyzes the Doppler readings to reconstruct the path of the arteries and detect potentially stenotic areas.

Doppler ultrasound system 12 is preferably a conventional pulsed Doppler system, which includes a transmitter that generates high frequency electronic signals that are amplified and output through at least one piezoelectric transducer. The transducer converts the signal from the transmitter into a wave of ultrasonic energy, which is directed toward a blood vessel for which blood flow information is desired. Moving blood cells reflect the ultrasound energy and either increase or decrease the frequency of the reflected energy depending on the direction of blood flow and the angle of incidence of the beam.

Although any appropriate Doppler system may be utilized, Doppler system 12 is preferably a B-mode and n-gated pulsed Doppler system that provides a bi-directional Doppler signal. Doppler ultrasound system 12 includes at least one transducer, but preferably includes a plurality of transducers. The use of a plurality of transducers provides multiple echo signals, which enable the velocity profile in the artery to be measured substantially simultaneously from multiple angles. This enables the system to determine the velocity profile with reduced error and also enables the system to more quickly scan the area under observation to speed the screening process. Each of the transducers is adapted to direct ultrasound waves typically in the order of 3–10 MHz, although any appropriate frequency or frequencies may be used, as desired, to enable improved system performance and detection. Initialization Procedure During the initialization procedure, a reference coordinate system is defined (13) relative to the patient's body for the purpose of recording the position of the Doppler scanner for every echo taken and the location of the echo received. This is important to enable the location of potentially stenotic arteries to be identified and stored during the screening process. With a known reference coordinate system, the test results using the system may be reproduced if necessary, and potentially stenotic areas may be located for imaging by a technician after screening and diagnosis. The paths of the arteries under investigation are later reconstructed based on the location and skew of each velocity profile measured.

The reference coordinate system is preferably defined by placing a mark or markers on the skin of the patient precisely positioned relative to a known anatomical feature on the patient, e.g., the collarbone, a rib, or the apex of the heart. Preferably at least two marks or anatomical features are used to define the reference coordinate system in order to ensure that the Doppler system can be positioned in the same position and orientation relative to the patient if necessary. Alternatively, the reference coordinate system may be defined relative to an anatomical feature that can be seen on the display of Doppler system 12 so that the Doppler scanner is initially positioned by a technician based on the location of the anatomical feature in a Doppler image generated by the scanner.

Once the reference coordinate system is defined, movements of the Doppler scanner(s) must be precisely measured relative to the coordinate system. Although the scanners of Doppler system 12 may be manually positioned and moved, a robotic system is preferably used to position the scanners.

Figure 8:
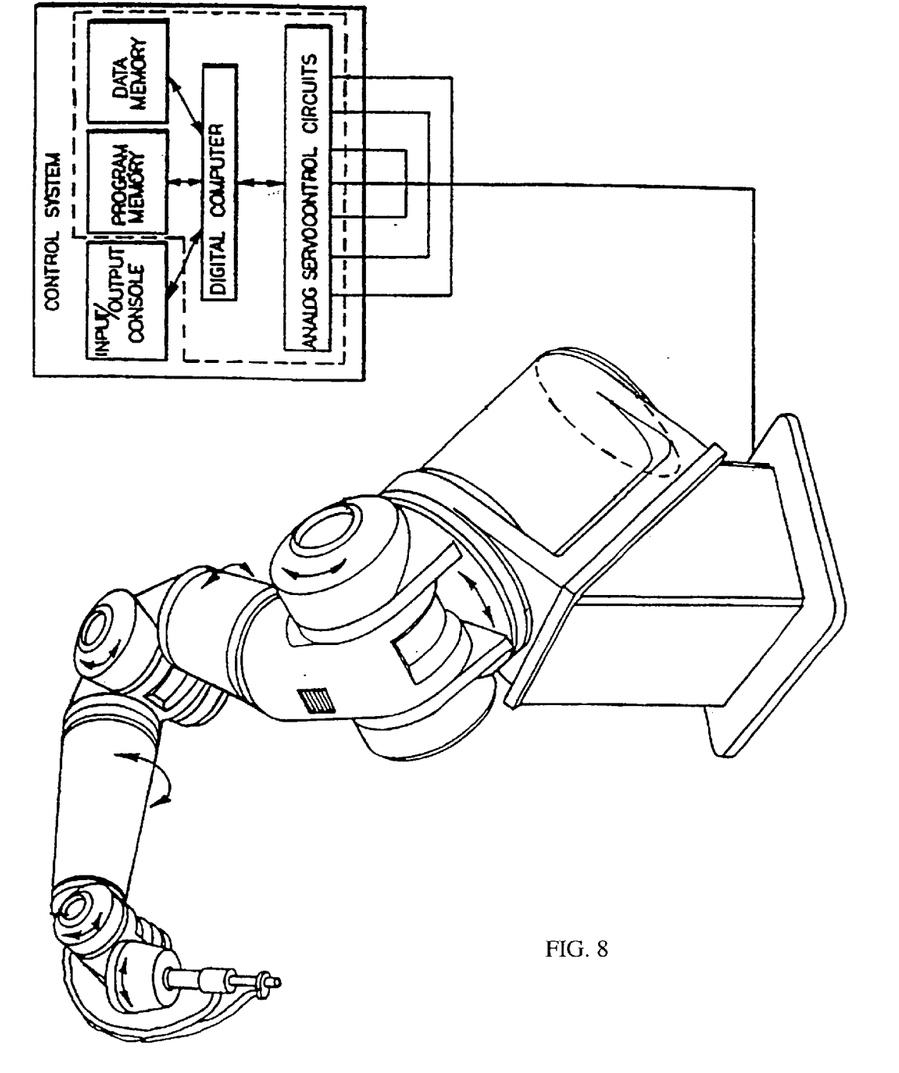
FIG. 8 is a schematic of a robotic device used to carry the system of the present invention.

Referring to FIG. 8, a potential carrier system for Doppler scanner 12 is exemplified in U.S. Pat. No. 4,975,856, the contents of which are incorporated herein by reference. This patent discloses a robotic arm with a servo or stepper motor that incrementally moves the scanner in a predetermined path without human intervention. Every joint on the arm has one or more motors and at least one potentiometer. The motors are used to move the scanner or scanners in a determined path during the screening procedure while the potentiometers simultaneously measure the position of the joints. The motors are controlled with a computer system connected via cables to the robotic arm. The scanner is held at the tip of the robotic arm.

The scanner may alternatively be a hand held scanner with a position sensor that measures the position of the scanner simultaneously with data collection. The readings from the potentiometers or from the hand held scanner are transferred to the computer system and are used for measuring and recording the position of each scan.

The robotic system is initially precisely positioned relative to the reference coordinate system. The robotic system then automatically moves or changes the relative angles of the scanners over the patient's body while scanning. For the purpose of defining the reference coordinate system, angles of reference measured on potentiometers of the robotic arm may be recorded and stored in memory 17. Alternatively, any appropriate system for measuring movement of the Doppler scanners may be utilized. The coordinates of every velocity profile measured are determined preferably based on the position of the scanner and the recall period of the Doppler echo.

Figure 1:
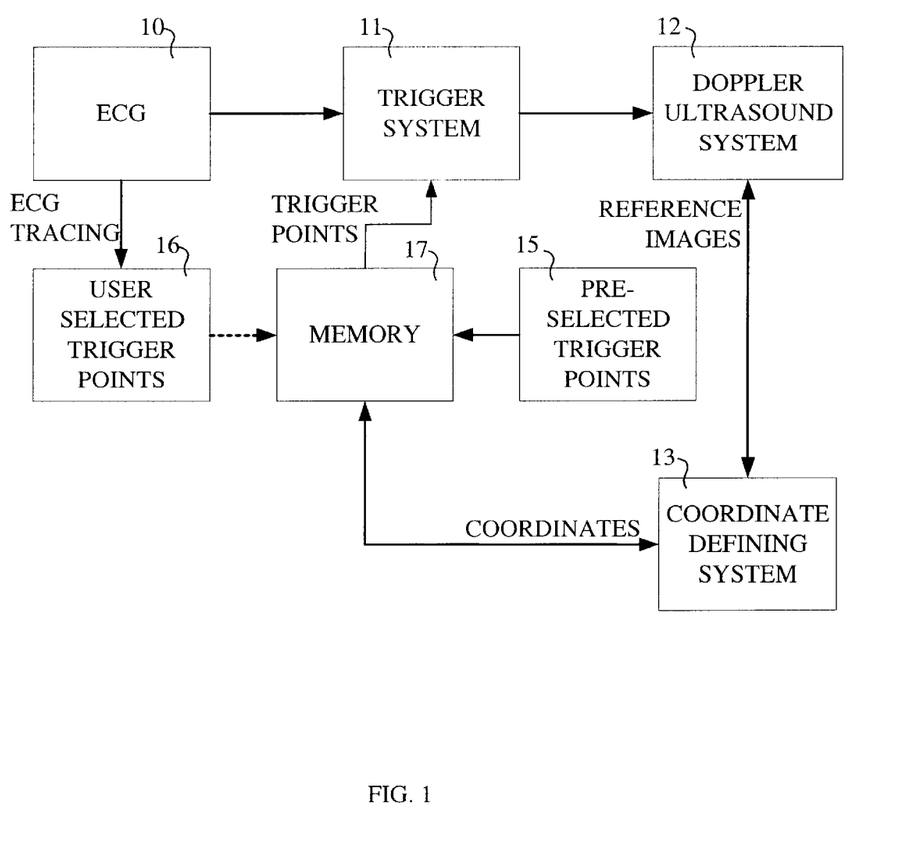
FIG. 1 is a block diagram of the initialization step of the system of the present invention.

Referring to FIG. 1, the heartbeat cycle of a patient is monitored by a traditional echocardiogram (ECG) system 10. ECG monitor 10 preferably displays the heartbeat cycle in predefined periodic timeframes. A trigger system 11 is connected to ECG monitor 10 and to Doppler system 12. Trigger system 11 is preferably a conventional controller or microprocessor-based device capable of detecting specified points along the ECG signal from ECG monitor 10. Trigger system 11 is programmed, for purposes of the screening procedure discussed in further detail below, to trigger Doppler system 12 at one or more specifically selected points in time along the heartbeat cycle of the patient, as monitored by ECG monitor 10.

The point at which the heart is at its maximum expansion, known as the diastole stage, is also the point where the heart is most electrically neutral. Points defined in the diastole stage of the heartbeat cycle are generally considered most appropriate for measuring blood flow through the coronary arteries via Doppler ultrasound because of the large measurable area of the heart. To record echoes at a specific stage in the heartbeat cycle, a point in time on an ECG cycle a specific distance from the peak of the R wave that would be indicative of that specific stage in the heartbeat cycle can be used as the trigger point for Doppler ultrasound system 12.

During the initialization process, one or more selected points within the ECG, and preferably within the diastole stage, are selected from an ECG trace 16 by the technician or physician and saved in memory 17. These selected points are used to trigger Doppler scanner 12 during the screening procedure. Alternatively, trigger system 11 may be preprogrammed to activate Doppler system 12 at any selected point 15 in the ECG cycle. The point or points 15, 16 selected during the initialization procedure are saved in memory 17 for use during screening. The selected points may also be predefined with no user interaction in the case of previously conducted procedures where the selected points along the heartbeat cycle were saved in memory 17 or in the case where triggering is always desired at the same trigger point in the ECG.

Screening and Diagnosis

Figure 2:
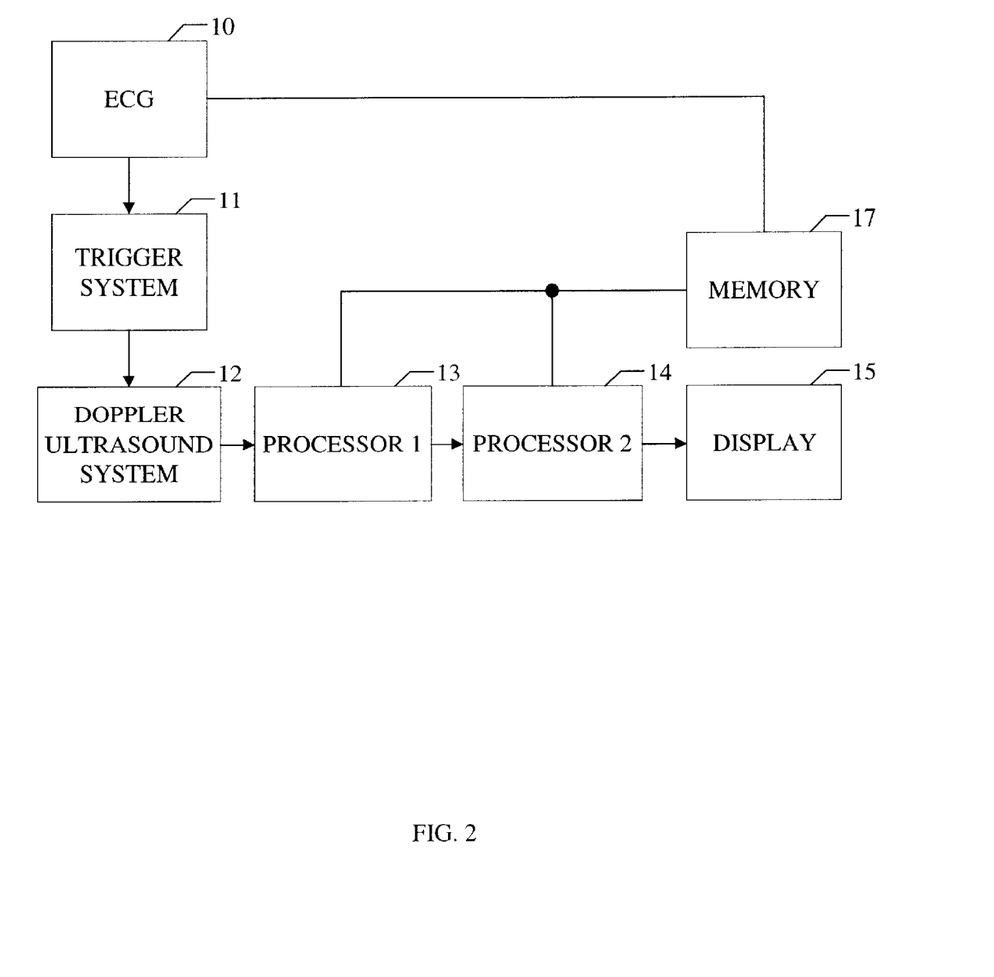
FIG. 2 is a block diagram of the screening step of the system of the present invention.

Referring generally to FIG. 2, during the screening procedure, Doppler scanner 12 automatically conducts repeated high-speed scans of an area with arteries within the reference coordinate system. These scans are conducted at varying positions and orientations relative to the patient in order to maximize the likelihood that stenotic arteries are viewed from an angle that will enable an accurate velocity profile and delta velocity profile to be determined. Because this determination is made without user intervention and without requiring the display and/or visual analysis of Doppler images, the scanning procedure may be conducted at high speeds. The diagnostic analysis to determine parameters indicative of potential stenotic arteries is conducted either during or after the screening procedure, preferably without user intervention.

Referring to FIG. 2, the system preferably includes two processors, i.e., first processor 13 and second processor 14. First processor 13 receives the echo signals from these numerous high speed scans and automatically determines the velocity profile (see FIG. 3) of blood flow within the artery and a series of parameters indicative of potential stenotic segments of arteries. During the diagnosis stage, these parameters are measured against selected thresholds by first processor 13, which automatically estimates the degree of stenosis based on the parameters measured and the relevant thresholds.

Second processor 14 provides numerous functions. Second processor 14 acts as an image processor that enables the user to view color Doppler ultrasound images using traditional methods, including using any available algorithms used to freeze cardiac motion. However, the present system automatically detects potentially stenotic areas without relying upon imaging by a technician. Thus, visual imaging is used only for secondary functions such as positioning the Doppler scanner within the reference coordinate system and manually imaging arteries determined by the system to be potentially stenotic.

Second processor 14 is also used to define and record the reference coordinate system and other parameters defined during initialization. During the screening procedure, second processor 14 records the position of the scanner for each scan performed and reconstructs the path of the arteries based on the coordinates and other parameters measured by first processor 13 for each velocity profile. Finally, second processor 14 defines and records the points in the heartbeat cycle that are used to trigger and activate the Doppler system.

Each of first processor 13 and second processor 14 is preferably a conventional microprocessor, although specialized controllers may be used if desired. Also first processor 13, second processor 14, trigger system 11 and/or other components of the system may be combined using an appropriate computer system.

In use, trigger system 11 detects the selected points in the heartbeat cycle that were defined in the initialization phase and activates the Doppler system 12 at the defined point in the heartbeat cycle. First processor 13 receives the Doppler signal from Doppler system 12 and identifies parameters v, dh, b, n, s, w as well as V, DH, B, N and S in the velocity profile for the blood vessels under consideration, as described in detail below. The coordinates are determined by second processor 14 and stored in memory 17. Upon completion of each scan, second processor 14 preferably moves the position of Doppler scanner 12 slightly by issuing appropriate commands to the robotic arm, at which point another scan is triggered by trigger system 11. Scanning of the entire region under consideration is made using any desired scanning pattern, e.g., side to side, sweeping angles, etc., until the entire area under consideration has been scanned from numerous positions and orientations. The coordinates together with the parameters measured for each velocity profile are used to reconstruct the path of the arteries present in the area of interest. Subsequently parameters $\Delta v/\Delta L$, $\Delta dh/\Delta L$, $\Delta b/\Delta L$, $\Delta n/\Delta L$, $\Delta s/\Delta L$, and $\Delta w/\Delta L$, and $(\Delta v/\Delta L)_a$, $(\Delta dh/\Delta L)_a$, $(\Delta b/\Delta L)_a$, $(\Delta dh/\Delta L)_a$, $(\Delta s/\Delta L)_a$, and $(\Delta w/\Delta L)_a$ can be determined and analyzed for the presence of stenosis in the arteries. In an alternate embodiment, upon completion of each scan, the Doppler signal measured can be stored in memory 17 with its corresponding coordinate point determined by second processor 14. At the termination of the scanning procedure all the parameters for each point in the coordinate system are analyzed to determine stenotic areas.

During or upon completion of the scanning process, first processor 13 automatically determines and analyzes the velocity profile through each detected artery to identify parameters indicative of stenosis, as discussed below. The locations of potentially stenotic areas are stored in memory 17 for later manual analysis by a technician or doctor. Since imaging is preferably not used for the initial detection of the stenosis, the scanning procedure is very rapid and the system is not limited in the amount of scans that it can perform during the screening procedure. If three Doppler beams are used simultaneously to record the velocity through an artery at different angles, the true angle of blood flow can be calculated with high precision and at high speed, and the degree of stenosis may be determined in percentage terms based on the measurements taken. Repeated scans of the area of interest at different angles decreases errors in the velocity profile and delta velocity profile measurements for a given segment of artery, thereby increasing the efficiency of diagnosis.

Parameters Indicative of Stenosis

Figure 3:
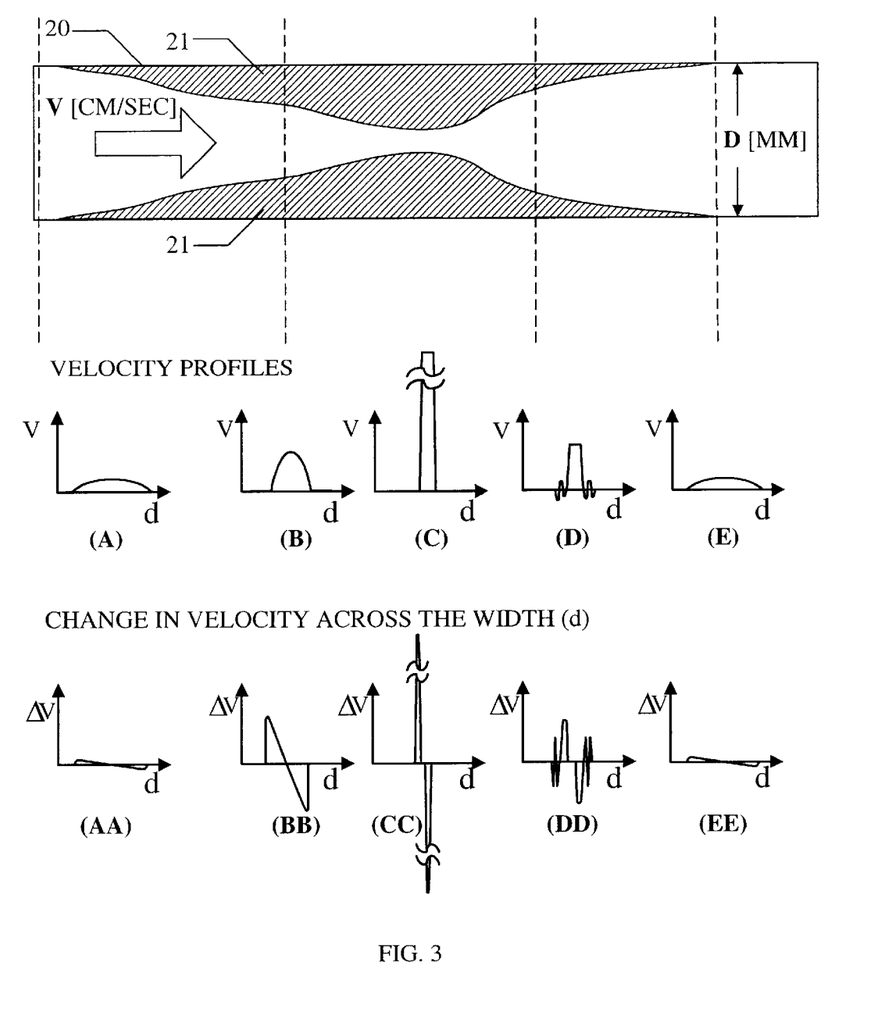
FIG. 3 is a schematic showing changes in a velocity profile across a stenotic artery with corresponding delta velocity profiles.

As shown in FIG. 3, a typical stenosis 21 is shown along with changes in the velocity profile as blood flows through an artery 20. As known in accordance with laminar flow theory, stable flow through a straight healthy coronary artery generally has a parabolic velocity profile. As the artery walls narrow due to a stenosis, the velocity of the blood flow increases with a magnitude that is proportional to the decrease of the diameter squared. For example, stenosis of about 80 to 85 percent results in a 25 times increase in velocity. This change may be readily detected when examining the velocity along the length of the vessel (see FIG. 3, profile C). Also shown below each of the velocity profiles (see FIG. 3, profiles AA to EE) are the velocity changes across each velocity profile with respect to the width of the velocity profile. The differential changes in velocity across the velocity profile CC have a more pronounced change in height due to stenosis as compared to the velocity profiles from which they are derived.

From the velocity of blood flow through an artery, which is detected by Doppler system 12, first processor 13 creates a velocity profile of the relevant segment of artery. By analyzing the velocity profile, first processor 13 generates certain parameters that are indicative of potentially stenotic segments of the artery, none of which alone necessarily indicates stenosis, but which in combination may indicate stenosis.

The average velocity v defined as the magnitude of average velocity across the measured velocity profile, is one such parameter that may be used to detect stenosis. This parameter can be normalized, as defined by parameter V, by dividing the measured average velocity v by the width of the velocity profile, w. Alternatively, the peak velocity or a weighted average velocity across the measured velocity profile can be used as a parameter to detect stenosis. As blood flows through a stenosis, the velocity increases and the width of the profile decreases. Parameter V is defined in Equation (1) as:

$$V=v/w \qquad (1)$$

Depending on the shape and the size of the stenosis, meaningful changes in the profile are first detected by an increase in the magnitude of the velocities of the parabolic profile, as is measured with parameter V, and later also by a change of shape. The acceleration that occurs through the stenosis causes the velocity profile to be blunter toward the center with a steeper change in velocity between the boundary layer and the blunt flow. This can be clearly seen when referring to the change in velocity across the velocity profile CC plotted in FIG. 3. Flow through a healthy artery is characterized in these profiles as two shallow triangles, positive and negative, that are attached as can be seen in profile AA of FIG. 3. As the vessel walls narrow due to stenosis, the triangles become steeper (profile BB). The maximum absolute peak defined by parameter dh is measure of the peak change in velocity between the boundary layer and the blunt flow. This parameter can be normalized by dividing it by the width, w of the velocity profile. Equation (2) defines the normalized parameter DH as follows:

$$DH=dh/w \qquad (2)$$

As the velocity profile becomes more blunt, the attached triangles separate and two separate peaks appear, positive and negative. This can be seen in profiles CC and DD. The distance between the two separated triangles, b can be used to characterize the blunt flow. This parameter can be normalized by dividing it by the width of the velocity profile and is defined by parameter B as follows:

$$B=b/w \qquad (3)$$

The typical rapid widening of the post-stenotic lumen results in turbulence in the post-stenotic region. Turbulence usually close to the artery wall, found at the exit of the stenosis is characterized by a noisy signal near the artery wall that may be seen on both the velocity profile D and in the change in velocity across the velocity profile DD. However, the small amplitude of the noisy signal shown on the velocity profile D is amplified and becomes readily visible in the delta velocity profiles DD. The degree of turbulence n found near the artery wall may be characterized by the root mean square (RMS) of the amplitude of the noisy signal measured at the boundary of the velocity profiles, n can alternatively be characterized in the frequency domain by the RMS of the amplitude of the power spectrum of the noisy signal. This parameter can be normalized by dividing it by the width of the velocity profile as follows:

$$N=n/w \qquad (4)$$

Thus, the characteristic of flow through a stenosis can be defined using the four parameters described above:
1. V defines the increase in velocity through a stenosis.
2. DH defines the increase in height between the velocity in the boundary layer and the peak velocity due to stenosis.
3. B measures the bluntness of the velocity profile flowing through the stenosis.
4. N defines the turbulence level at the boundary layer at the exit of the stenosis.

If any of these parameters exceed a defined threshold, the area is considered potentially stenotic. A combination of the relative values of these parameters, and/or changes in these parameters along the length of an artery, can also serve to define a suspected stenotic region.

Figure 4:
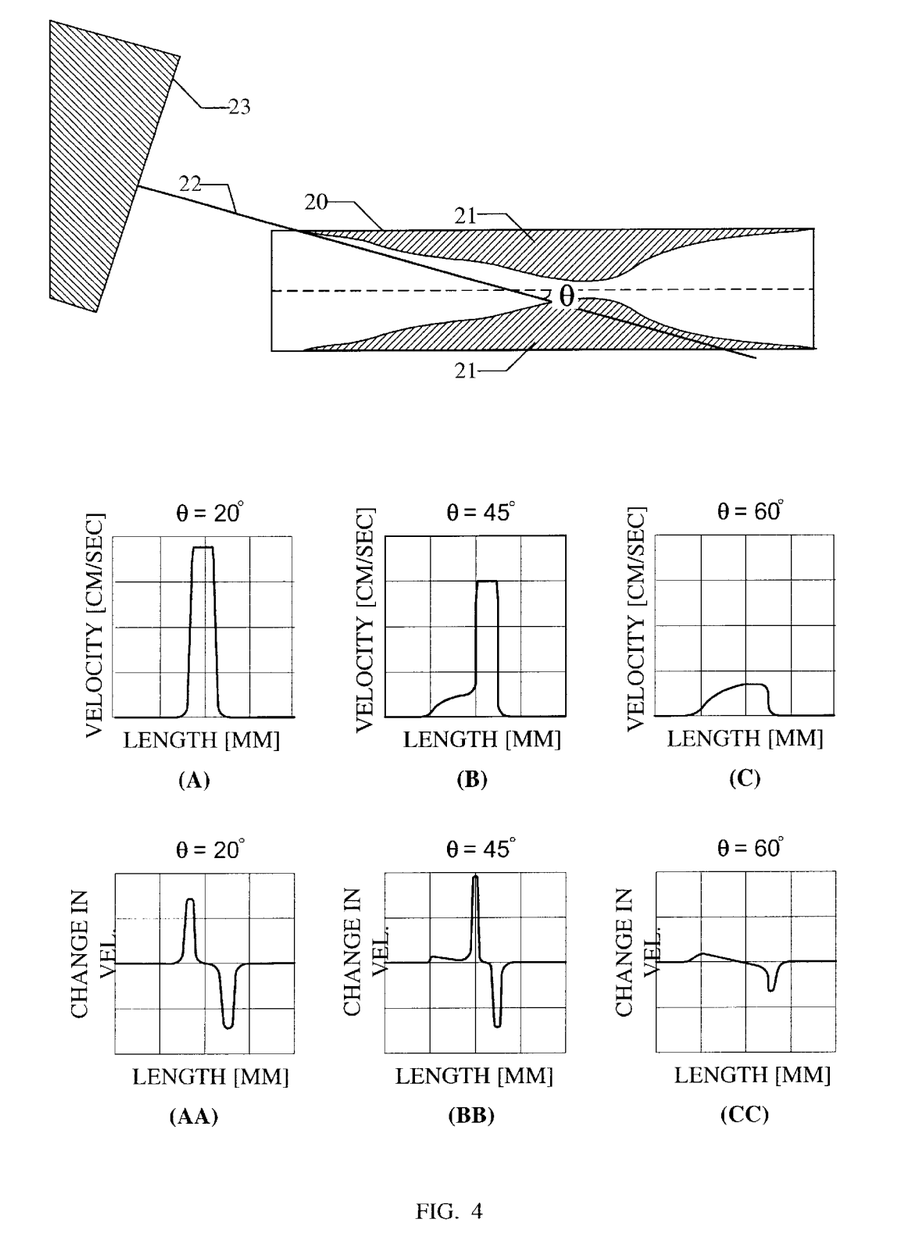
FIG. 4 shows example velocity profiles derived using the system of the present invention.

When a Doppler ultrasound beam 22, shown in FIG. 4, is directed by Doppler transmitter 23 at some angle with respect to the blood flow direction, the velocity profile that is detected is the projection of the velocity measured in the blood flow. In this case, the velocity profile will not only be lower in amplitude, due to the projection, but may also be "smeared" since the shape of the velocity changes significantly as the blood flows through the stenosis 21. An example of this is shown in FIG. 4. When measuring at a 20° offset, the general shape of the velocity profile recorded through the narrow portion of the stenosis is maintained as can be seen from profile A. However, the amplitude is reduced to a degree proportional to the cos θ, and the width of the profile is increased to a degree proportional to 1/cos θ. As shown in FIG. 4, as the offset angle increases, the width of the velocity profile measured increases while the amplitude decreases. This is shown in profiles B and C. As an example, a profile may increase in width by about 50 percent when measured at an offset angle of 60°, as shown in profile C. In addition, as the offset angle increases, the profile begins to "smear" and data from wider and narrower portions of the stenosis are incorporated in the one profile. This is shown in profiles B and C. The profiles showing the change in velocity, AA to CC, show that the peaks occur as long as even a portion of the jet stream is captured. However, the profiles appear smeared due to the offset angle.

Profiles with beam offsets of 20° and 45° (profiles AA and BB respectively) may be identified by measuring the height of the peaks (positive and negative) on the curve showing how the velocity changes across the velocity profile, while at 60° (profile CC), the peak cannot be readily identified. Although stenosis cannot be detected at all beam offsets, the system is designed to scan the same sample area at a number of different angles and from a number of different positions, so that in at least one position the stenosis may be identified, i.e., the offset angle will be sufficiently small, and marked as a potential site for stenosis.

Velocity profiles are examined not only for their amplitude but also for their width and general shape. This ensures that the system can distinguish between different coronary arteries. Healthy coronary arteries with diameters of about 1 to 3 mm have a flow rate about 30 to 50 cm/sec with a parabolic velocity profile. Other larger arteries can be associated with blood flow at higher velocities and with blunter velocity profiles but with diameters significantly larger than that of coronary arteries. Constricted flow in a stenotic artery can be distinguished from flow in a healthy artery with a diameter similar to the stenotic region by comparing the shape of the velocity profiles and the magnitude of the peak velocities. As blood flows downstream to smaller arteries, the blood flow velocity decreases due to an increase in the total cross section of vessels used to transport the blood. In a stenotic region the velocity increases through the constricted area. In addition, as mentioned above, the jet stream occurring through a stenotic region results in a velocity profile that is blunt compared to the parabolic velocity that is present in healthy coronary arteries.

Figure 5:
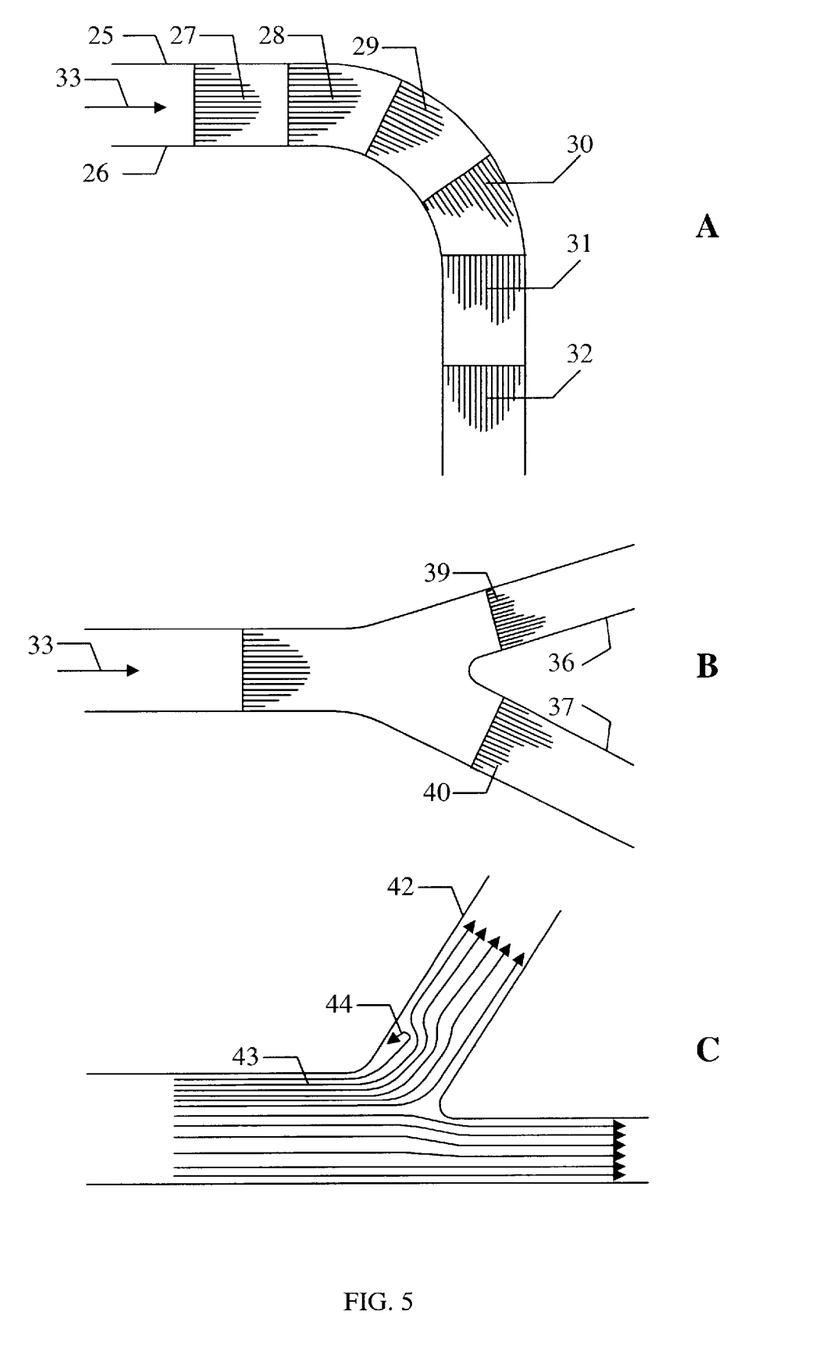
FIGS. 5A–5C are schematics showing changes in velocity profiles due to curvature and bifurcations in an artery.
Figure 6A:
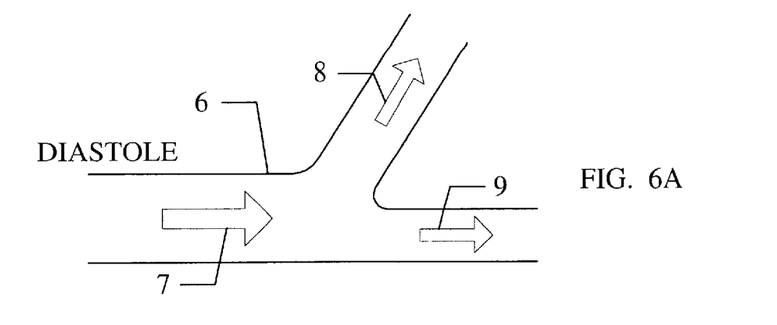
FIGS. 6A–6D are schematics showing the direction of flow in a healthy artery versus an occluded artery during the diastole and systole stages of the heart cycle.
Figure 6B:
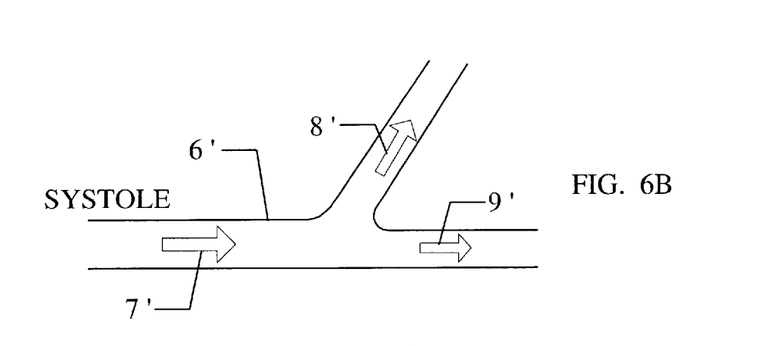
Figure 6C:
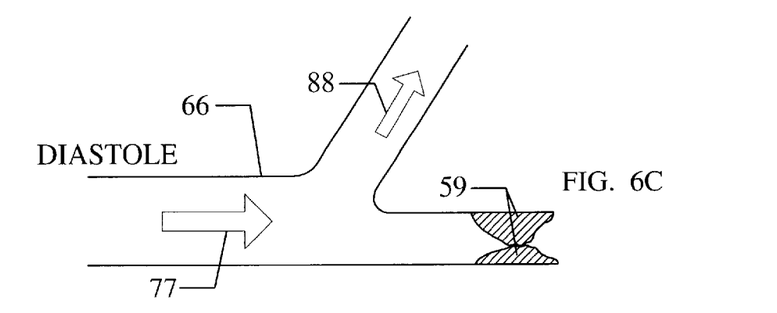
Figure 6D:
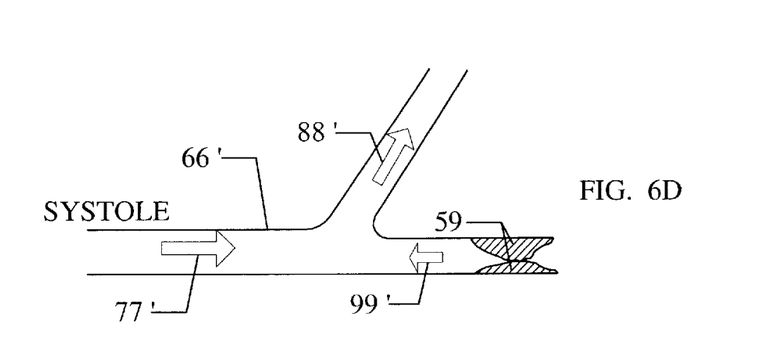

The known parabolic velocity profile occurring in healthy arteries following a straight path may be altered significantly due to curved arteries. Coronary arteries tend to curve as they follow along the surface of the heart and lead away from the main arteries to nourish the myocardium. FIG. 5A shows a schematic of changes in the velocity profile due to curvature of the blood vessel. The velocity profile 27 prior to the curvature is assumed to be parabolic. As the blood flow 33 approaches the curved segment, the velocity profile (28, 29, 30) is skewed toward the outer wall of the vessel 25, while the inner wall 26 is left with a relatively low wall shear stress. As the blood exits the curved segment the velocity profile 31 begins to skew toward the center again and eventually returns to its original parabolic shape 32. Although the shape of the velocity profile can change significantly as the blood flows through a curved section of a vessel, the flow normally stays laminar. The relatively higher wall stress seen by a sharp change in velocity that occurs in the outer wall in a curved section during laminar flow may be differentiated from the much higher wall stresses or sharper change in velocity that occur when a jet stream of blood passes a stenotic segment of vessel. A similar occurrence can be seen at a bifurcation point shown in FIG. 5B. The velocity profile downstream from a bifurcation point (39, 40) is skewed toward the inner walls of the smaller vessels, 36 and 37 respectively. The shape of the velocity profile depends on the angle of curvature. Flow curves 43 are shown in FIG. 5C. For a large angle of curvature, back flow, 44 can occur near the outer wall 42 of the smaller vessels. This area is a potential area where the appearance of stenosis can occur but is not an indication of stenosis itself.

A skew level parameter s may be defined that is a measure of the distance that the peak velocity is off-center from the centerline of flow in a curved vessel. A skew toward the right of the centerline can be taken as a positive skew and a skew toward the left of the centerline can be taken as a negative skew. This parameter can be normalized by dividing it by the width of the velocity profile measured, w. The normalized parameter S is therefore defined as:

$$S = s/w \tag{5}$$

The skew level parameter along with other parameters associated with the shape of each velocity profile measured can be used to define the direction of blood flow, which in turn can be used to reconstruct the path of each artery based on the direction of blood flow at different points in the defined coordinate system. Once reconstruction of the arterial path is accomplished, the change in parameters v, dh, b, n, s, and w over the length of the artery can be defined. Peaks above a defined threshold in any or in a group of the parameters, $\Delta v/\Delta L$, $\Delta dh/\Delta L$, $\Delta b/\Delta L$, $\Delta n/\Delta L$, $\Delta s/\Delta L$, and $\Delta w/\Delta L$, and $(\Delta v/\Delta L)_a$, $(\Delta dh/\Delta L)_a$, $(\Delta b/\Delta L)_a$, $(\Delta n/\Delta L)_a$, $(\Delta s/\Delta L)_a$, and $(\Delta w/\Delta L)_a$ can be used as an indication of stenosis. The width of a peak that is identified can be used to define the width of potential stenotic region.

An artery that is completely occluded can be identified by comparing the direction of flow in the area of the occlusion during the diastole and systole stages. FIGS. 6A–6D show schematically the direction of flow in a healthy artery versus an occluded artery during the diastole and systole stage of the heart cycle. In the case of a healthy artery 6, blood will flow in the downstream direction 7, 8, and 9 through all channels during the diastole stage. The same will occur during the systole stage although the diameter of the arteries decreases due to contraction of the myocardium where the coronary arteries are embedded. Where part of an artery is occluded due to stenosis 59, blood will flow in the downstream direction 77 and 88 through the open arteries. In this case, when only observing flow during the diastole stage, the occlusion may not be detected since there is no flow through the clogged artery. However, in the same location 66' during the systole stage, the contraction of the myocardium leads to back flow 99' in the area of the occlusion 59. Such back flow during the systole stage that is absent in the diastole stage may be an indication of coronary occlusion in the artery.

Figure 7:
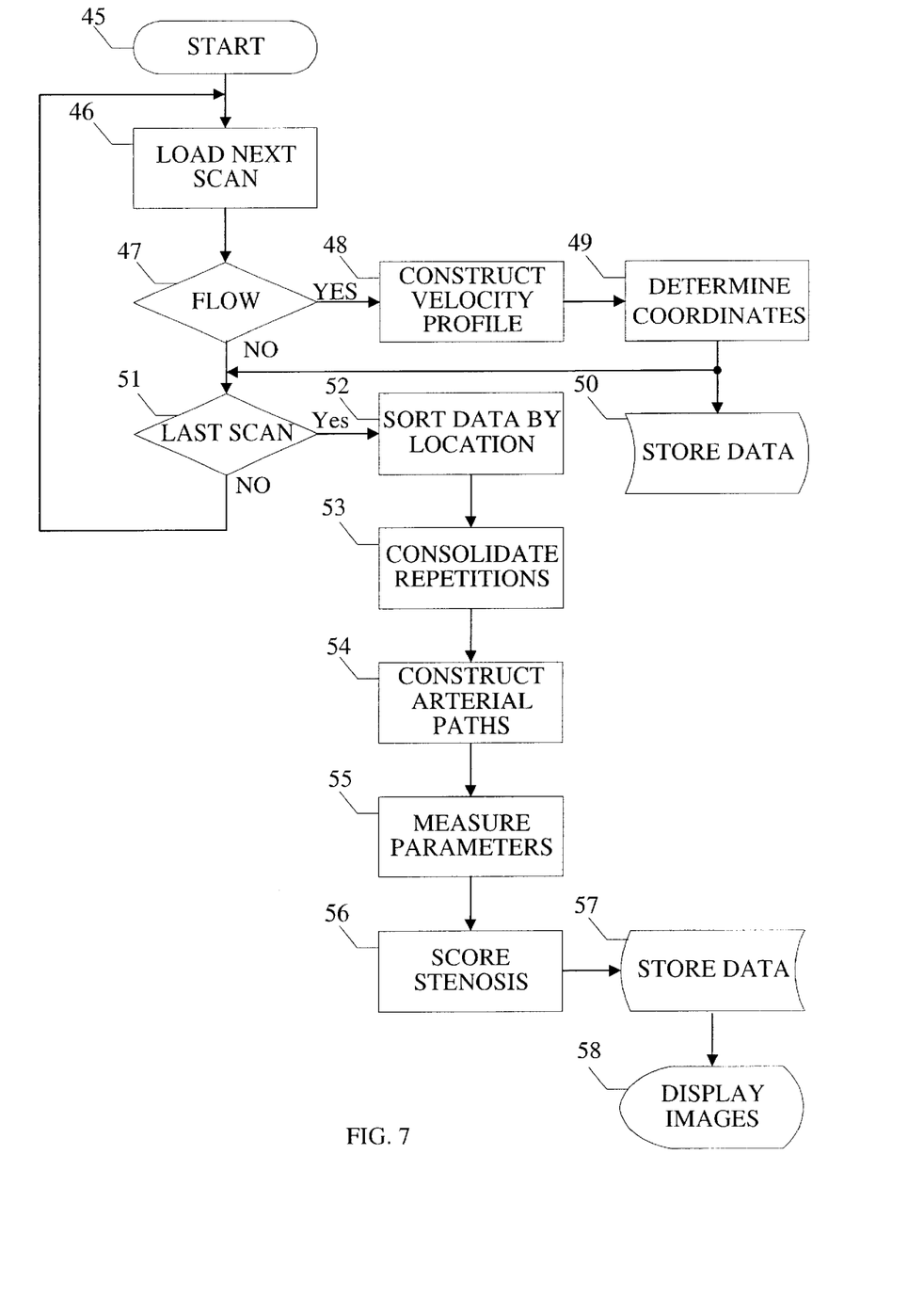
FIG. 7 is a flow chart of the screening step of the system of the present invention.

FIG. 7 shows a flow chart describing the procedure for using the system of the invention to perform stenosis screening. The system is first used to perform a scan or scans of the target area as described above. These scans may either be stored and then analyzed in a batch, or processed as the scans are taken. For each target area scanned, first processor 13 detects the presence of flow in the area (47). If flow is detected, first processor 13 constructs a velocity profile (48) of the relevant artery and the location of the scan is identified (49) by second processor 14. Data defining the velocity profile and the coordinates of the artery under examination is stored (50) for later reference. Upon completion of the screening procedure (51), the data defining the velocity profile of each echo is sorted by location (52) in the defined coordinate system. If more than one echo was recorded in a specific location, the echo that best represents the velocity profile at that point is chosen. This determination may be based on the amplitude and coherency of the velocity profile constructed from the different echoes recorded, from the signal-to-noise ratio, or from some other criteria. Beginning with one point in the defined coordinate system, the adjacent area is scanned for a second velocity profile that most closely matches the previous scan in regard to direction of flow, skew or other characterizing features of the velocity profile. This procedure is repeated as required to determine a path of the artery under consideration (54). The system then determines any or all of the parameters described above with respect to the individual velocity profiles measured, and their changes along the length of the artery (55). Scores relating to potentially stenotic areas are then determined based on the parameters measured (56). Potentially stenotic areas and their corresponding scores are stored (57) and prepared for display (58) for further analysis.

Scoring the degree of stenosis may be determined using any appropriate technique. For example, score (56) may be defined by parameter DH, where dh is measured in centimeters per second over millimeters and the width of velocity profile, w, measured in millimeters. An alternative scoring system may be parameter V where v is measured in centimeters per second and w is measured in millimeters.

Using an average diameter for a healthy coronary artery of 2 mm and an average healthy flow rate of 40 cm/sec, a healthy V score would be in the range of 20. A stenosis that is shorter than 5 mm in length, defined by 50 percent blockage would have a velocity of close to 160 cm/sec and a width of close to 1 mm. This would result in a score of close to 160. A stenosis defined by 80 percent blockage would result in a velocity of about 1,000 cm/sec with a width of about 0.4 cm. This would result in a score of about 25,000. Using such a scoring system, as an example, a score representing a stenosis of below 25% may be considered a mild stenosis. A score representing a stenosis between 25% and 65% may be considered a significant stenosis. A score representing a stenosis of above 65% may be considered a severe stenosis. Of course, any desired categorization of stenosis may be utilized. Table 1 lists scores using the scoring system described above corresponding to different percent stenosis.

TABLE 1

| % Stenosis | Diameter [mm] | Velocity [cm/sec] | Score (0° offset) | Score (45° offset) |
|---|---|---|---|---|
| 0% | 2 | 40 | 20 | 10 |
| 25% | 1.5 | 71 | 47 | 23 |
| 50% | 1 | 160 | 160 | 80 |
| 65% | 0.7 | 327 | 467 | 233 |
| 80% | 0.4 | 1000 | 25000 | 12500 |

These scores are valid assuming an offset angle of zero. However, it is more realistic to assume a normal distribution of offset angles between 0 to 90 degrees with an average offset angle of 45°. To account for this offset angle, the velocities measured are assumed to be reduced by cos (45°) and the widths of the profile measured are assumed to be enlarged by 1/cos (45°). In this case, in the scoring system described above the ratio of the velocity over the width of the profile must be multiplied by $\cos^2$ (45°) or 0.5 before dividing the scores into groups of mild, significant, and severe stenosis. When using parameter DH to score the stenosis, the difference between the scores for different degrees of stenosis is even more pronounced. This is because the change in amplitude as is shown in FIGS. 3 and 4 is much more pronounced and therefore the resolution may be higher.

Analysis of the data may be performed during and after the scanning procedure is completed. The delta velocity profile may be defined as the change in any one of the parameters (v, dh, b, n, s, w) measured with respect to the length or width of the reconstructed artery, as appropriate, i.e., across or along the artery. Scores along with all the parameters measured may be displayed and/or the scans may temporarily be saved in memory until the analysis is performed. Doppler ultrasound images of the areas saved in memory may also be displayed and examined visually to determine the severity of the stenosis.

In addition to having first processor 13 automatically determine the degree of stenosis of the segment of artery under consideration, conventional imaging using a monitor 15 may be used to further analyze the degree of stenosis and its effect on blood flow at the end of the screening procedure. Monitor 15 is preferably a simple PC monitor to view images obtained from Doppler system 12. Using monitor 15, the user may point to different positions on the image, and the position in the reference coordinate system may be recorded in memory 17, or alternatively, marked visually on the screen. At the end of the screening procedure, the stored points of abnormality and other marked positions may be retrieved from memory 17 and displayed on monitor 15 for further direct examination. All relevant data recorded in the area of interest may be displayed in the image on monitor 15, including the parameters measured, coordinates, point on the heartbeat cycle observed via ECG monitor the degree of stenosis, etc. The user may also choose to manually rescan areas of interest for further analysis.

It will be appreciated that while the system of the invention has been described with respect to detection of the parameters V, DH, B, N, S, v, dh, b, n, s and w, and their change along the length of the artery $\Delta v/\Delta L$, $\Delta dh/\Delta L$, $\Delta b/\Delta L$, $\Delta n/\Delta L$, $\Delta s/\Delta L$, and $\Delta w/\Delta L$, and $(\Delta v/\Delta L)_a$, $(\Delta dh/\Delta L)_a$, $(\Delta b/\Delta L)_a$, $(\Delta n/\Delta L)_a$, $(\Delta s/\Delta L)_a$, and $(\Delta w/\Delta L)_a$, these parameters are only examples of parameters indicative of stenosis that may be utilized by the invention, and any other such parameters are within the scope of the invention. More generally, although the present invention has been described with respect to certain embodiments and examples, variations exist that are within the scope of the invention as described in the following claims.

What is claimed is:

1. A method of detecting stenosis of an artery comprising the steps of:
   scanning each point in a reference coordinate system in an area of interest using a plurality of Doppler ultrasound transducers, wherein, at each point, each of the plurality of Doppler ultrasound transducers takes measurements of blood flow substantially simultaneously from a different angle from the other of the plurality of Doppler ultrasound transducers; and
   analyzing the measurements of blood flow to determine potentially stenotic areas within an artery.

2. The method according to claim 1, further comprising the step of:
   determining an orientation of each of the plurality of the Doppler ultrasound transducers in the reference coordinate system upon detecting potentially stenotic areas within the artery.

3. The method according to claim 2, further comprising the step of measuring angles of reference between one or more of the transducers and a selected reference point.

4. The method according to claim 1, further comprising the step of positioning at least one scanner relative to the area of interest for detecting stenosis thereof.

5. The method according to claim 4, further comprising the step of positioning a plurality of scanners relative to the area of interest for detecting stenosis thereof.

6. The method according to claim 1, further comprising the step of constructing a delta velocity profile of blood flow along the length of the artery.

7. The method according to claim 1, wherein the step of analyzing the blood flow comprises the steps of:
measuring at least one parameter indicative of a potentially stenotic artery; and
determining from the at least one measured parameter whether stenosis may be present in the artery.

8. The method according to claim 7, wherein the at least one parameter is selected from the group consisting of V, DH, B, N, S, v, dh, b, n, s and w.

9. The method according to claim 7, wherein the at least one parameter is compared with a predefined threshold value to determine potentially stenotic areas within the artery.

10. The method according to claim 7 further comprising scoring the degree of stenosis and determining coordinates of the potentially stenotic artery.

11. The method according to claim 7, further comprising the steps of sorting the measured parameters and consolidating repetitive information.

12. The method according to claim 1, further comprising carrying at least one of the plurality of transducers on a robotic arm.

13. The method according to claim 1, further comprising the step of triggering scanning based on a window in an ECG of the patient.

14. The method according to claim 1, further comprising the step of reconstructing a path of the artery for detecting stenosis over a length of the artery.

15. The method according to claim 1, further comprising the step of analyzing a velocity profile to determine potentially stenotic areas within the artery by comparing velocity profiles of the artery in the systole stage to velocity profiles of the artery in the diastole stage.

16. The method according to claim 1, further comprising the step of analyzing a velocity profile to determine potentially stenotic areas within the artery by comparing a direction of flow in the potentially stenotic area in the systole stage and the diastole stage.

17. The method of claim 1, further comprising the step of constructing a velocity profile of blood flow within the artery.

18. The method of claim 1, further comprising the steps of:
constructing a velocity profile and delta velocity profile of the blood flow in the artery; and
based on the velocity profile and delta velocity profile, identifying potentially stenotic areas in the artery.

19. The method according to claim 18 further comprising the steps of:
using the velocity profile and delta velocity profile to determine parameters selected from the group consisting of V, DH, B, N, S, v, dh, b, n, s ,w, $\Delta v/\Delta L$, $\Delta dh/\Delta L$, $\Delta b/\Delta L$, $\Delta n/\Delta L$, $\Delta s/\Delta L$, $\Delta w/\Delta L$, $(\Delta v/\Delta L)_a$, $(\Delta dh/\Delta L)_a$, $(\Delta b/\Delta L)_a$, $(\Delta n/\Delta L)_a$, $(\Delta s/\Delta L)_a$, and $(\Delta w/\Delta L)_a$; and
comparing one or more of the parameters with predefined threshold values to determine potentially stenotic areas within the artery.

20. An apparatus for detecting stenosis of an artery, which comprises:
a Doppler system for scanning each point in a reference coordinate system in an area of interest and for receiving a plurality of Doppler echoes substantially simultaneously from multiple different angles from blood flow in an artery in the area of interest; and
a processor for receiving signals representative of the echoes and for constructing a velocity profile of blood flow through the segment of artery, the processor analyzing the velocity profile to determine potentially stenotic areas within the artery.

21. The apparatus according to claim 20, wherein the processor is adapted to determine a location of the Doppler ultrasound system in the reference coordinate system.

22. The apparatus according to claim 20, wherein the Doppler ultrasound system comprises a plurality of scanners.

23. The apparatus according to claim 21, further comprising means for measuring angles of reference between one or more scanners of the Doppler ultrasound system and a selected reference point in the reference coordinate system.

24. The apparatus according to claim 20, wherein the processor constructs a delta velocity profile of blood flow through arteries present in the area of interest.

25. The apparatus according to claim 20, wherein the processor detects at least one parameter indicative of the presence of stenosis.

26. The apparatus according to claim 25, wherein at least one parameter indicative of the presence of stenosis is selected from the group consisting of V, DH, B, N, S, v, dh, b, n, s, w, $\Delta v/\Delta L$, $\Delta dh/\Delta L$, $\Delta b/\Delta L$, $\Delta n/\Delta L$, $\Delta s/\Delta L$, $\Delta w/\Delta L$, $(\Delta v/\Delta L)_a$, $(\Delta dh/\Delta L)_a$, $(\Delta b/\Delta L)_a$, $(\Delta n/\Delta L)_a$, $(\Delta s/\Delta L)_a$, and $(\Delta w/\Delta L)_a$.

27. The apparatus according to claim 25, wherein the processor compares the parameter with a predefined threshold value to determine potentially stenotic areas within the artery.

28. The apparatus according to claim 20 further comprising a robotic arm for carrying the Doppler ultrasound system.

29. The apparatus according to claim 20 further comprising:
means for measuring a plurality of parameters indicative of a potentially stenotic artery;
means for determining from the measured parameters the degree of stenosis in the artery; and
means for scoring the degree of stenosis and determining coordinates of the potentially stenotic artery.

30. The apparatus according to claim 20, further comprising a trigger for detecting a window in an ECG of the patient and for triggering scanning by the Doppler ultrasound system based on detection of the window.

31. The apparatus according to claim 21, wherein the processor reconstructs the path of at least a portion of the artery.

32. The apparatus according to claim 20, further comprising:
means for constructing a velocity profile and a delta velocity profile of the blood flow in the artery; and
means for identifying potentially stenotic areas in the artery based on the velocity profile and delta velocity profile.

33. The apparatus according to claim 32 further comprising:
means for using the velocity profile and delta velocity profile to determine at least one parameter selected from the group consisting of V, DH, B, N, S, v, dh, b, n, s w, $\Delta v/\Delta L$, $\Delta dh/\Delta L$, $\Delta b/\Delta L$, $\Delta n/\Delta L$, $\Delta s/\Delta L$, $\Delta w/\Delta L$, $(\Delta v/\Delta L)_a$, $(\Delta dh/\Delta L)_a$, $(\Delta b/\Delta L)_a$, $(\Delta n/\Delta L)_a$, $(\Delta s/\Delta L)_a$, and $(\Delta w/\Delta L)_a$; and
means for comparing one or more of the parameters with predefined threshold values to determine potentially stenotic areas within the artery.

34. The apparatus of claim 20, further comprising a means of constructing a velocity profile of blood flow within the artery.

* * * * *